(12) United States Patent
Matsuura et al.

(10) Patent No.: US 7,883,527 B2
(45) Date of Patent: *Feb. 8, 2011

(54) ANNULOTOMY CLOSURE DEVICE AND RELATED METHODS

(75) Inventors: David G. Matsuura, Encinitas, CA (US); Walter D. Gillespie, La Mesa, CA (US); James F. Marino, La Jolla, CA (US); Selise M. Pastore, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 92 days.

This patent is subject to a terminal disclaimer.

(21) Appl. No.: 11/982,253

(22) Filed: Oct. 31, 2007

(65) Prior Publication Data

US 2008/0140108 A1 Jun. 12, 2008

Related U.S. Application Data

(60) Continuation of application No. 11/078,541, filed on Mar. 11, 2005, which is a division of application No. 09/663,250, filed on Sep. 15, 2000, now Pat. No. 6,964,674.

(60) Provisional application No. 60/154,969, filed on Sep. 20, 1999.

(51) Int. Cl.
  *A61B 17/08* (2006.01)
  *A61B 17/70* (2006.01)
  *A61F 2/44* (2006.01)
(52) U.S. Cl. .................. 606/213; 623/17.12; 623/17.16
(58) Field of Classification Search ................ 606/151, 606/213, 72, 246, 247, 248, 249; 623/17.12, 623/17.15, 17.16; 128/898
See application file for complete search history.

(56) References Cited

U.S. PATENT DOCUMENTS

| 3,867,728 A | 2/1975 | Stubstad et al. |
| 3,872,861 A | 3/1975 | Tamny et al. |
| 3,874,388 A | 4/1975 | King et al. |
| 3,875,595 A | 4/1975 | Froning |
| 4,788,788 A | 12/1988 | Brockett |
| 4,817,643 A | 4/1989 | Olson |

(Continued)

FOREIGN PATENT DOCUMENTS

WO  9531948  11/1995

(Continued)

OTHER PUBLICATIONS

International Search Report from Int'l Application PCT/US00/25678, (3 pages).

(Continued)

*Primary Examiner*—Darwin P Erezo
*Assistant Examiner*—Jing Rui Ou
(74) *Attorney, Agent, or Firm*—Jonathan Spangler; Rory Schermerhorn

(57) ABSTRACT

A system for sealing a hole in a body, comprising a generally cylindrical mesh formed from a plurality of helical strands which is inserted into the hole, with at least one end of the cylindrical mesh being moved least partially through an interior portion of the cylindrical shaped mesh such that the mesh expands radially outwards against sides of the hole.

13 Claims, 13 Drawing Sheets

U.S. PATENT DOCUMENTS

| | | | |
|---|---|---|---|
| 5,061,274 | A | 10/1991 | Kensey |
| 5,095,897 | A | 3/1992 | Clark et al. |
| 5,108,404 | A | 4/1992 | Scholten et al. |
| 5,133,733 | A | 7/1992 | Rasmussen et al. |
| 5,192,326 | A | 3/1993 | Bao |
| 5,334,217 | A | 8/1994 | Das |
| 5,370,660 | A | 12/1994 | Weinstein et al. |
| 5,413,571 | A | 5/1995 | Katsaros et al. |
| 5,540,715 | A | 7/1996 | Katsaros et al. |
| 5,549,679 | A | 8/1996 | Kuslich |
| 5,571,189 | A | 11/1996 | Kuslich |
| 5,601,562 | A | 2/1997 | Wolf et al. |
| 5,674,241 | A | 10/1997 | Bley et al. |
| 5,681,310 | A | 10/1997 | Yuan et al. |
| 5,725,552 | A | 3/1998 | Kotula et al. |
| 5,733,294 | A | 3/1998 | Forber et al. |
| 5,846,261 | A | 12/1998 | Kotula et al. |
| 5,860,992 | A | 1/1999 | Daniel et al. |
| 5,904,713 | A | 5/1999 | Leschinsky |
| 5,944,739 | A | 8/1999 | Zlock et al. |
| 5,976,174 | A | 11/1999 | Ruiz |
| 6,033,428 | A | 3/2000 | Sardella |
| 6,036,720 | A | 3/2000 | Abrams et al. |
| 6,090,116 | A * | 7/2000 | D'Aversa et al. ............ 606/151 |
| 6,168,622 | B1 | 1/2001 | Mazzocchi |
| 6,206,921 | B1 | 3/2001 | Guagliano et al. |
| 6,224,630 | B1 * | 5/2001 | Bao et al. ................ 623/17.16 |
| 6,245,107 | B1 * | 6/2001 | Ferree ........................ 606/279 |
| 6,293,960 | B1 | 9/2001 | Ken |
| 6,312,465 | B1 | 11/2001 | Griffin et al. |
| 6,334,865 | B1 | 1/2002 | Redmond et al. |
| 6,371,990 | B1 | 4/2002 | Ferree |
| 6,402,750 | B1 | 6/2002 | Atkinson et al. |
| 6,419,704 | B1 | 7/2002 | Ferree |
| 6,425,919 | B1 | 7/2002 | Lambrecht |
| 6,425,924 | B1 | 7/2002 | Rousseau |
| 6,428,576 | B1 | 8/2002 | Haldiman |
| 6,454,804 | B1 | 9/2002 | Ferree |
| 6,468,303 | B1 | 10/2002 | Amplatz |
| 6,482,235 | B1 | 11/2002 | Lambrecht et al. |
| 6,508,839 | B1 | 1/2003 | Lambrecht et al. |
| 6,579,291 | B1 | 6/2003 | Keith et al. |
| 6,592,625 | B2 | 7/2003 | Cauthen |
| 6,645,247 | B2 | 11/2003 | Ferree |
| 6,648,920 | B2 | 11/2003 | Ferree |
| 6,652,585 | B2 | 11/2003 | Lange |
| 6,689,125 | B1 | 2/2004 | Keith et al. |
| 6,712,853 | B2 | 3/2004 | Kuslich |
| 6,719,797 | B1 | 4/2004 | Ferree |
| 6,736,815 | B2 | 5/2004 | Ginn |
| 6,783,546 | B2 | 8/2004 | Zucherman et al. |
| 6,805,695 | B2 | 10/2004 | Keith et al. |
| 6,835,205 | B2 | 12/2004 | Atkinson et al. |
| 6,852,128 | B2 | 2/2005 | Lange |
| 6,878,167 | B2 | 4/2005 | Ferree |
| 6,883,520 | B2 | 4/2005 | Lambrecht et al. |
| 6,936,072 | B2 | 8/2005 | Lambrecht et al. |
| 6,964,674 | B1 | 11/2005 | Matsuura et al. |
| 2002/0007218 | A1 | 1/2002 | Cauthen |
| 2002/0111688 | A1 | 8/2002 | Cauthen |
| 2002/0120337 | A1 | 8/2002 | Cauthen |
| 2002/0123807 | A1 | 9/2002 | Cauthen |
| 2002/0147497 | A1 | 10/2002 | Belef et al. |
| 2002/0151979 | A1 | 10/2002 | Lambrecht et al. |
| 2002/0151980 | A1 | 10/2002 | Cauthen |
| 2002/0156532 | A1 | 10/2002 | Ferree |
| 2002/0156533 | A1 | 10/2002 | Ferree |
| 2002/0165542 | A1 | 11/2002 | Ferree |
| 2002/0189622 | A1 | 12/2002 | Cauthen |
| 2003/0004574 | A1 | 1/2003 | Ferree |
| 2003/0009227 | A1 | 1/2003 | Lambrecht et al. |
| 2003/0014117 | A1 | 1/2003 | Lambrecht et al. |
| 2003/0014118 | A1 | 1/2003 | Lambrecht et al. |
| 2003/0033017 | A1 | 2/2003 | Lotz et al. |
| 2003/0040796 | A1 | 2/2003 | Ferree |
| 2003/0050702 | A1 | 3/2003 | Berger |
| 2003/0093155 | A1 | 5/2003 | Lambrecht et al. |
| 2003/0110688 | A1 | 6/2003 | Prescott |
| 2003/0120345 | A1 | 6/2003 | Cauthen |
| 2003/0125807 | A1 | 7/2003 | Lambrecht et al. |
| 2003/0153976 | A1 | 8/2003 | Cauthen |
| 2003/0158604 | A1 | 8/2003 | Cauthen |
| 2003/0163200 | A1 | 8/2003 | Cauthen |
| 2003/0181983 | A1 | 9/2003 | Cauthen |
| 2003/0187507 | A1 | 10/2003 | Cauthen |
| 2003/0187508 | A1 | 10/2003 | Cauthen |
| 2003/0191536 | A1 | 10/2003 | Ferree |
| 2003/0220690 | A1 | 11/2003 | Cauthen |
| 2003/0220693 | A1 | 11/2003 | Cauthen |
| 2003/0220694 | A1 | 11/2003 | Cauthen |
| 2004/0010317 | A1 | 1/2004 | Lambrecht et al. |
| 2004/0024465 | A1 | 2/2004 | Lambrecht et al. |
| 2004/0030392 | A1 | 2/2004 | Lambrecht et al. |
| 2004/0034429 | A1 | 2/2004 | Lambrecht et al. |
| 2004/0044412 | A1 | 3/2004 | Lambrecht et al. |
| 2004/0097924 | A1 | 5/2004 | Lambrecht et al. |
| 2004/0097980 | A1 | 5/2004 | Ferree |
| 2004/0172019 | A1 | 9/2004 | Ferree |
| 2004/0186573 | A1 | 9/2004 | Ferree |
| 2004/0260286 | A1 | 12/2004 | Ferree |
| 2004/0260397 | A1 | 12/2004 | Lambrecht et al. |
| 2005/0004578 | A1 | 1/2005 | Lambrecht et al. |
| 2005/0033440 | A1 | 2/2005 | Lambrecht et al. |
| 2005/0033441 | A1 | 2/2005 | Lambrecht et al. |
| 2005/0038519 | A1 | 2/2005 | Lambrecht et al. |
| 2005/0060038 | A1 | 3/2005 | Lambrecht et al. |
| 2005/0149197 | A1 | 7/2005 | Cauthen |
| 2005/0155612 | A1 | 7/2005 | Matsuura |
| 2005/0206039 | A1 | 9/2005 | Lambrecht et al. |
| 2005/0240269 | A1 | 10/2005 | Lambrecht et al. |
| 2008/0071301 | A1 | 3/2008 | Matsuura et al. |

FOREIGN PATENT DOCUMENTS

| | | |
|---|---|---|
| WO | 0110316 A1 | 2/2001 |
| WO | 0112107 A1 | 2/2001 |
| WO | 0128464 A1 | 4/2001 |
| WO | 02054978 A2 | 7/2002 |
| WO | 02054978 A3 | 7/2002 |
| WO | 03011155 A2 | 2/2005 |

OTHER PUBLICATIONS

Written Opinion from Int'l Application PCT/US00/25678, (4 pages).
International Search Report from Int'l PCT/US00/25678, (3 pages).
Wake, Warren K. Design Paradigms: A source Book for Creative Visualization. John Wiley & Sons, Inc. 2000. p. 192-193.

* cited by examiner

ANNULOTOMY CLOSURE DEVICE AND RELATED METHODS

CROSS-REFERENCES TO RELATED APPLICATIONS

The present application is a continuation of U.S. patent application Ser. No. 11/078,541, filed Mar. 11, 2005, which is a divisional of U.S. patent application Ser. No. 09/663,250 filed Sep. 15, 2000, now issued as U.S. Pat. No. 6,964,674, which claims benefit under 35 U.S.C. §119(e) from U.S. Provisional Application Ser. No. 60/154,969, filed on Sep. 20, 1999, the complete disclosures of which are hereby incorporated herein by reference in their entirety for all purposes.

BACKGROUND OF THE INVENTION

I. Field of the Invention

The present invention relates to systems for sealing holes in body parts and to sealing surgically formed holes in a bony structure in general and in particular to systems for providing closure of a surgical access hole in an intervertebral disc following an annulotomy.

II. Description of the Related Art

Each intervertebral disc has a firm outer layer, called the annulus fibrosus, and a gelatinous interior called the nucleus pulposus. The annulus fibrosus acts as a semi-rigid elastic pressure vessel to contain the nucleus pulposus, therefore creating a compliant interface between the relatively rigid vertebrae above and below each disc. Adjacent to each disc, a pair of nerve roots pass from the spinal canal through apertures called intervertebral foramen on each side of the spine. Due to the location of the nerve roots, they are vulnerable to pressure from a herniated disc. In certain instances, the herniated section of the annulus fibrosus may become thinner through the transverse plane of the disc.

When a partial intervertebral discectomy is performed, the offending portion of the herniated disc is excised. In this procedure, the surgeon must first make an appropriate incision through the skin and other tissue layers, and then typically create an access hole into the herniated annulus (an annulotomy) to treat the offending tissue. Such access holes are created with a variety of surgical instruments including scalpels, probes, trephines, etc., and the access hole may range in size from 3 to 6 mm in diameter. Furthermore, as instruments are passed through the circular hole, the hole may become enlarged or elongated in nature upon completion of the procedure. Upon entry to the interior annular space, the offending tissue is then manipulated and/or removed by the surgeon. In current practice, the surgeon closes the outer wounds created by the procedure, but leaves the access hole open. Due to the semi-rigid nature of the annular tissue, closure by means of traditional tissue approximation techniques, such as suturing, is nearly impossible. Closure is further complicated by the proximity of nerves and the depth of the access hole below the surface of the skin. As a complication of disc excision surgery, such annular defects can represent a potential liability with respect to subsequent recurrent disc herniations. This is due to the fact that the annular defect between the interior space of the annulus and the area adjacent to the annulotomy allows for possible future passage of nucleus pulposus tissue therethrough. During the course of normal movement by the patient during the post operative healing phase, (which may last up to several weeks), relatively high fluidic pressures can be generated within the annular space. These high pressures can cause the nucleus pulposus to be extruded through the open hole and impinge upon nearby nerves, thus causing a reoccurrence of the original symptoms that the surgeon intended to treat.

SUMMARY OF THE INVENTION

The present invention provides methods and apparatus for the closure of holes, including surgical access holes formed in a rigid or semi-rigid body, and is particularly useful in closing a surgical access hole in an intervertebral disc. As such, the present invention provides systems of annulotomy closure which reduce the risks of reherniation.

In a first aspect of the invention, a system comprising a generally cylindrical-shaped mesh is used to seal a hole which may be a surgical access hole. The mesh itself may preferably comprise a braid of separate strands with each strand following a helical path around a central longitudinal axis such that the mesh comprises a flexible tube of interwoven springs. In various optional aspects, at least one of the proximal (i.e.: outer surface) and distal (i.e.: deep) ends of the cylindrical-shaped mesh may optionally be covered by an end-cap which may be made of the mesh material.

In this first aspect of the invention, the mesh cylinder may first be inserted into the hole in the annulus and positioned such that both the proximal and distal ends of the mesh extend somewhat out of the respective proximal and distal ends of the hole. Thereafter, the proximal end of the mesh can be pushed longitudinally in a distal direction through the "interior" of the mesh (i.e.: through the central tube defined by the cylindrically-shaped mesh body) to a distance such that the proximal end may pass fully through the interior of the mesh, and extend in a distal direction at least partially past the distal end of the mesh. This causes the mesh cylinder to become folded over upon itself, with one end of the mesh being folded into the center of the mesh.

In further aspects, the distal end of the cylindrical-shaped mesh may be pulled in a proximal direction such that a region of the mesh adjacent the distal end expands radially outwards, bulging around the inner (distal) perimeter of the distal end of the hole. Furthermore, the proximal end of the cylindrical mesh can be pushed in a distal direction such that a portion of the mesh adjacent the proximal end of the hole expands radially outwards, bulging around the outer (proximal) perimeter of the hole.

The present invention also provides a method of sealing a hole in a body part, comprising introducing a generally cylindrical shaped mesh into the hole and then moving at least one end of the cylindrical shaped mesh at least partially through an interior portion of the cylindrical shaped mesh such that the mesh expands radially outwards against sides of the hole.

The pushing of the proximal end in a distal direction and/or the pulling of the distal end in proximal direction will preferably tend to cause the cylindrical shaped mesh to expand radially outwards, thereby firmly anchoring the mesh against the walls of the hole in the annulus.

In further preferred aspects, the proximal and distal ends of the cylindrical mesh can be formed to be of a fixed diameter such as by the attachment or formation of a non-expandable ring thereon.

A plurality of suture/tethers may optionally be attached to the distal end of the mesh to pull it in a proximal direction. Tubular inserters for positioning the cylindrical mesh within the bore of the hole may also be provided.

In various aspects, the diameter of one end of the mesh is constructed to be smaller than that of the other end of the mesh such that a first end can easily be pulled through a second end of the mesh. In specific preferred aspects, the diameter of the proximal end will be smaller than that of the distal end.

In an alternate method of employing the present invention, each of the proximal and distal ends of the cylindrical mesh may be pulled partially into the center of the cylindrical mesh (ie: pulled partially through the interior tube defined by the mesh body) such that the proximal end is moved distally and the distal en if moved proximally, towards, or optionally passing through, one another.

In a second aspect of the invention, various systems for sealing a surgically cut hole in the disc are provided comprising a generally planar sheet-like material which is cut or formed into a circular pattern having a plurality of radially extending "flower petal"-type extensions. These petals are first bent radially inwards giving the structure a generally conical shape. The petals will then tend to flex radially outwards when released after the device has been place into the hole in the annulus, thereby sealing the hole. Specifically, the resultant conical structure of the second aspect of the invention is inserted longitudinally into the hole in the annulus and is then released such that the petals will tend to flex radially outwards, thereby anchoring the structure in position in the hole. In this aspect of the invention, the spaces cut between successive radially extending petals may be adapted to permit some fluid movement therethrough. In various designs of this aspect of the invention, a plurality of such sheet-like "flower petal" structures are bent into a conical shape and are inserted in succession into the hole.

Advantages of both aspects of the present invention include its encouragement of rapid healing by providing a lattice structure to enhance tissue growth. Moreover, the present annulotomy closure systems are also able to accommodate the various sizes and geometries of annular holes that may be encountered by the surgeon. Furthermore, the present annulotomy closure systems all provide compensation for normal movement during patient healing since the system itself remains transversely flexible but is positionally stable along its longitudinal axis. A further advantage of the present system is that should any portion of the mesh remain on the outside of the hole on the annulus, this would be atraumatic to adjacent nerves in close proximity to the device due to the soft and flexible nature of the mesh material.

DESCRIPTION OF THE SPECIFIC EMBODIMENTS

The present invention provides methods and apparatus for sealing holes in various bony structures. In a preferred aspect, the present invention provides methods and apparatus for sealing a surgical hole drilled in a patient's annulus. As such, the present invention is ideally suited to seal a hole drilled in an intervertebral disc such that nucleus pulposus on the inside of the disc is compressed during normal movement. The present system is not limited only to sealing holes which have been drilled in an annulus, but may also be used to seal naturally occurring holes as well. Moreover, the present invention is not limited to sealing holes in the annulus alone but may be used to seal any hole, thereby inhibiting the passage of soft tissue therethrough.

Figure 1:
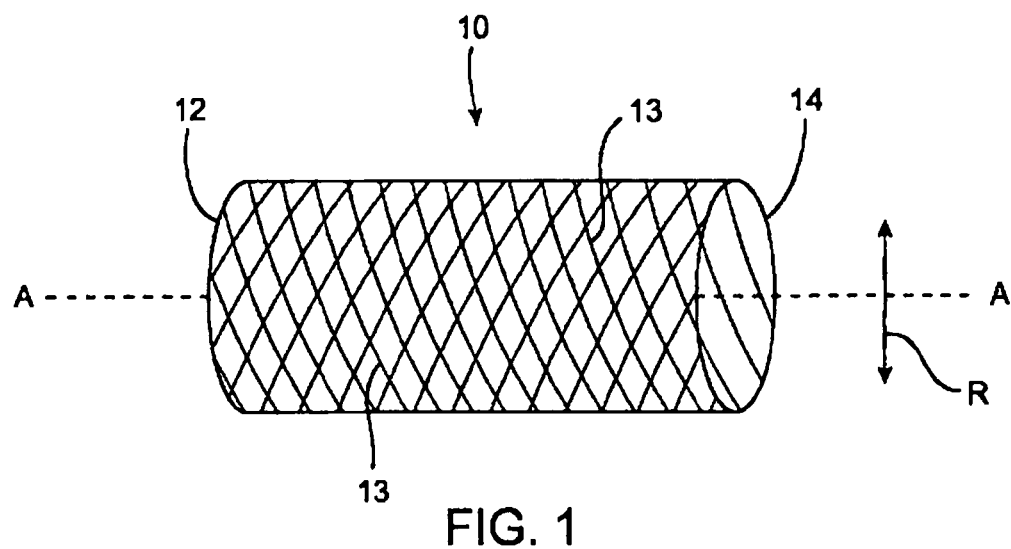
FIG. 1 is a perspective view of a cylindrical shaped mesh.

FIG. 1 shows a generally cylindrical tubular mesh which is comprised of a multiplicity of monofilament or multifilliar strands 13 of suture-type material, each following a helical path about central longitudinal axis A. Mesh 10 has a proximal end 12 and a distal end 14. An advantageous property of mesh 10 is that as proximal end 12 and distal end 14 are moved closer together with respect to one another, mesh 10 will tend to expand radially outwards, widening in its diameter D.

In a preferred design, the mesh diameter D is approximately 1 to 8, millimeters, and more preferably about 3 millimeters when mesh 10 is in its relaxed state, (i.e.: when ends 12 and 14 are not being pushed together). When ends 12 and 14 are pushed together, however, diameter D of mesh 10 may reach 9 millimeters. In preferred designs, strands 13 may each be made of 0.15 millimeter polypropylene sutures. Other materials having suitable dimensions, bioabsorption, strength, spring rate or radiopacity may also be used.

In an optional aspect, proximal end 12 may be sealed, for example with a mesh closure positioned thereover. In another optional aspect of the invention, as will be explained, ends 12 and 14 may be formed to be non-expandable such that their diameters do not change as ends 12 and 14 of mesh 10 are pushed together relative to one another. For example, a solid ring may be formed at, or attached to, one or both of ends 12 and 14.

Figure 2:
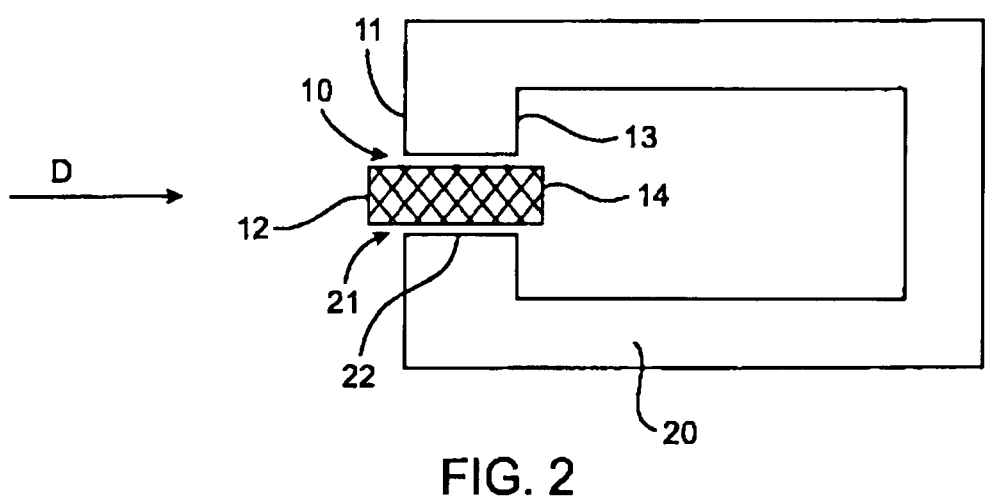
FIG. 2 is a sectional side elevation view of the cylindrical mesh of FIG. 1 positioned in a hole in the annulus of an intervertebral disc.

FIG. 2 illustrates a preferred method of operating the present invention, as follows. Mesh 10 is inserted longitudinally in distal direction D into surgically cut hole 21 in disc 20 such that proximal end 12 and distal end 14 extend out of hole 21 past outer surface 11 and inner surface 13 of hole 21 in disc 20 as defined by walls 22 as shown.

Figure 3:
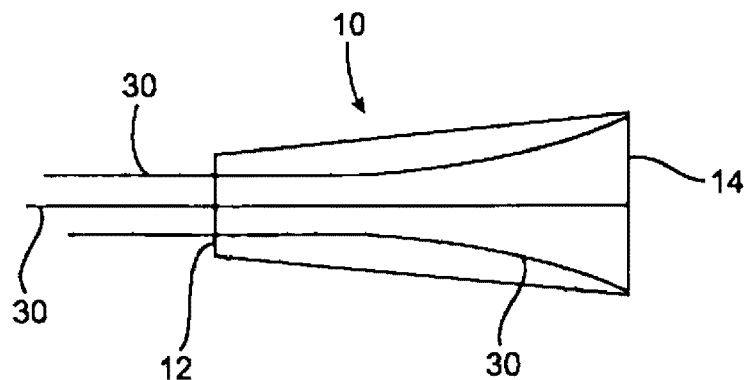
FIG. 3 is a sectional side elevation view of a tubular shaped mesh.

As is shown in FIG. 3, mesh 10 may optionally be fitted with a plurality of sutures/tethers 30 which are tied to the distal end 14 of mesh 10 and extend through the central chamber of mesh 10 as shown.

Figure 4:
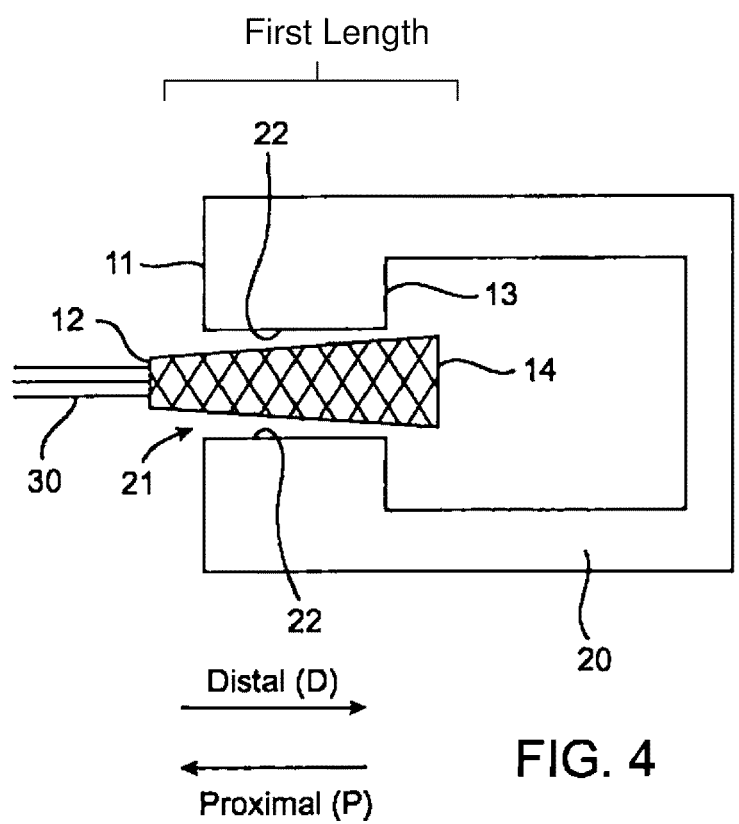
FIG. 4 is a sectional side elevation view of the mesh of FIG. 3 received through a hole in an intervertebral disc.

As shown in FIG. 4, mesh 10 is inserted in a distal direction D such that it is positioned in hole 21 with its distal end 14 extending past inner surface 13 of disc 20, and with its proximal end 12 extending past outer surface 11 of disc 20. The placement of distal end 14 at an appropriate distal depth such that a portion of mesh 10 extends in a proximal direction from outer surface 11 of hole 21 can be enhanced through various visualization techniques such as shaft depth markers or endoscopic, radiographic or ultrasound methods.

For clarity of illustration, to show both the side walls of hole 21 and mesh 10, the following Figs. show a small clearance between the walls of the mesh and the walls of the hole when the mesh has been expanded into position, (for example, by pushing proximal end 12 and distal end 14 together, or through the central longitudinally extending chamber of the mesh). It is to be understood that such clearance would not exist as mesh 10 becomes anchored against walls 22 when positioned.

Figure 5:
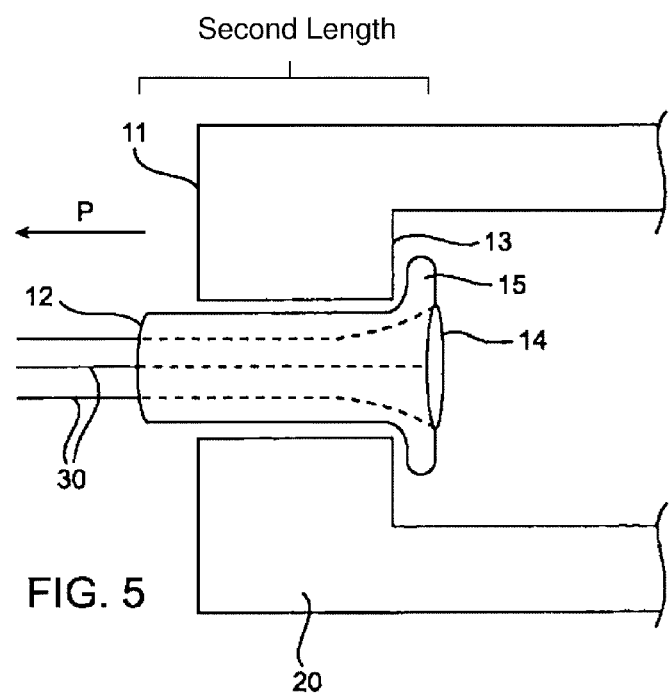
FIG. 5 is the system of FIG. 4 after the distal end of the mesh has been pulled in a proximal direction, causing a portion of the mesh to expand around the inner surface of the hole.

Following the step shown in FIG. 4, suture tethers 30 are preferably pulled in proximal direction P while proximal end 12 is held in a fixed position relative to hole 21, (as shown in FIG. 5). When pulled by suture/tethers 30, distal end 14 will tend to move in proximal direction P such that mesh 10 will expand radially in diameter in the region of the mesh pushing outwardly against the inner surface of hole 21, and forming a bulge 15 at mesh distal end 14 against inner surface 13.

Figure 6:
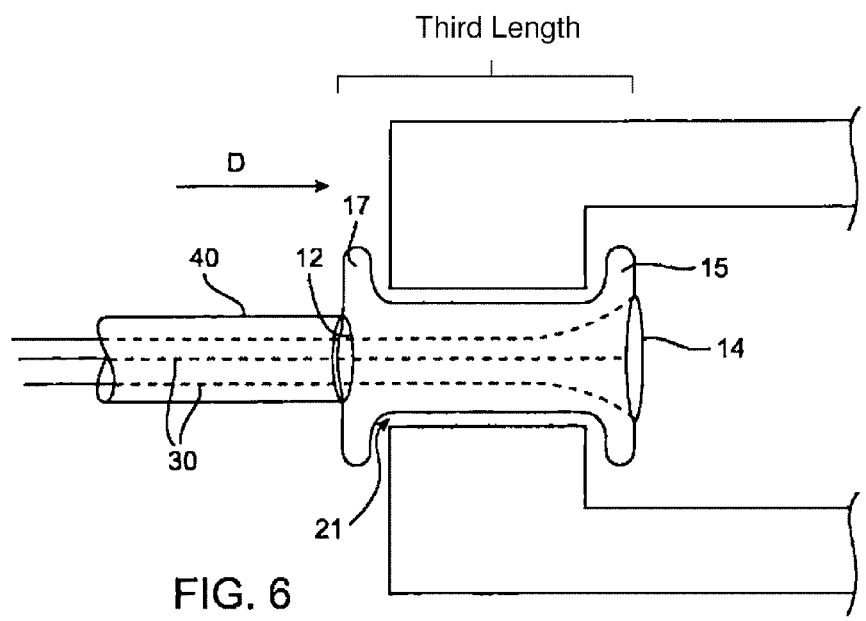
FIG. 6 shows the system of FIG. 4 after the proximal end of the mesh has been pushed in a distal direction, causing a portion of the mesh to expand around the outer surface of the hole.

Thereafter, as is shown in FIG. 6, a rod 40, (which can be used to hold proximal end 12 in position relative to hole 21 while pulling on suture tethers 30 as illustrated in FIG. 5), can be used to push proximal end 12 in distal direction D such that the region of mesh 10 between proximal end 12 and outer surface 11 will tend to expand around the proximal end of hole 21, forming a bulge 17 against outer surface 11, as shown. In this aspect of the invention, proximal end 12 may optionally be formed to be non-expandable, for example by attachment to a fixed diameter ring therearound.

The effect of mesh 10 being deformed to form respective bulges 17 and 15 at the outer surface 11 and inner surface 13 of disc 20 will be to hold mesh 10 at a fixed longitudinal position relative to hole 21 (such that it doesn't move in either a proximal or distal direction).

Figure 7:
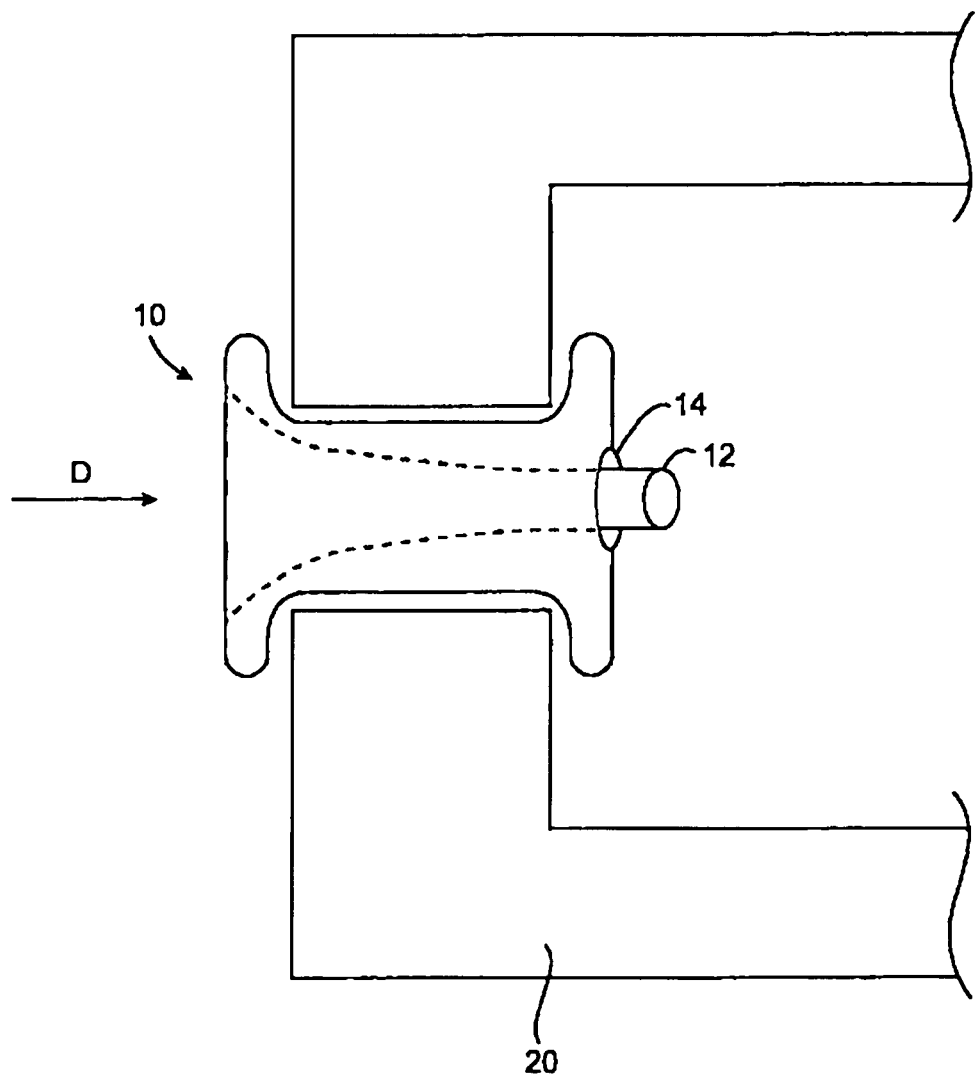
FIG. 7 shows the system of FIG. 6 after the proximal end of the mesh has been pushed distally through the distal end of the mesh.

Thereafter, as is shown in FIG. 7, proximal end 12 may optionally be pushed longitudinally in distal direction D such that is passes through the center of the mesh such that it extends out through distal end 14. In this aspect of the invention, proximal end 12 may be formed to be non-expandable and have a slightly larger diameter than that of distal end 14 such that distal end 12 can pass through distal end 14 and be snap-fit through the opening of proximal end 14.

Figure 8:
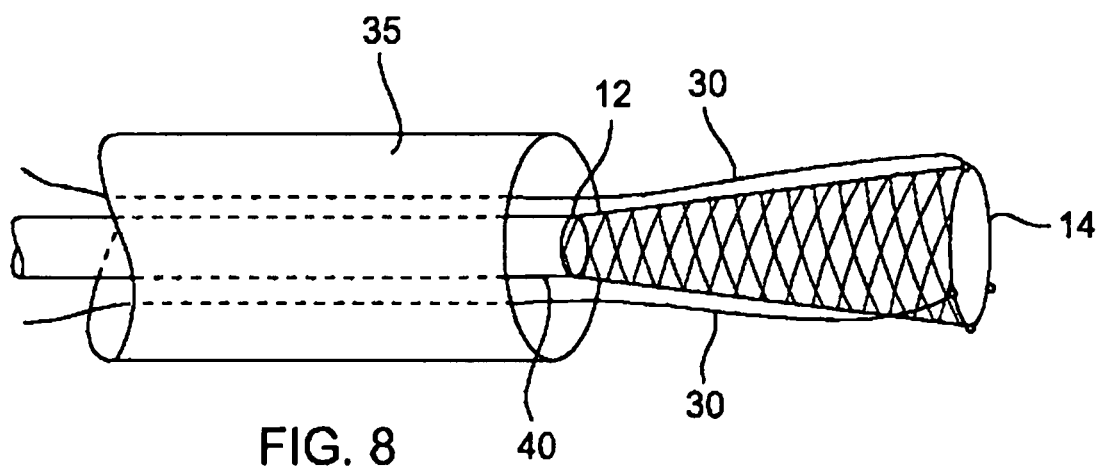
FIG. 8 is a perspective view of a system for delivering the tubular mesh illustrated in FIGS. 3 to 7.

FIG. 8 is a perspective view of a system for delivering and positioning mesh 10 into hole 21 of the disc 20 as illustrated in FIGS. 1 to 7. Rod 40 may be used to support proximal end 12 at a fixed position relative to hole 21 when suture/tethers 30 are used to pull distal end 14 in a proximal direction. In addition, rod 40 can be used to push proximal end 12 through distal end 14, as was shown in FIG. 7. Suture/tethers 30 which may preferably comprise three tethers anchored to distal end 14 at locations which are spaced radially 120° apart may be received over push rod 40 as shown. A tubular inserter 35 is then received thereover. Inserter 35 may be used for pushing mesh 10 against the proximal end of hole 21 as is shown in FIG. 6 so as to create bulge 17. Suture tethers 30 may preferably be cut or removed after insertion.

Figure 9:
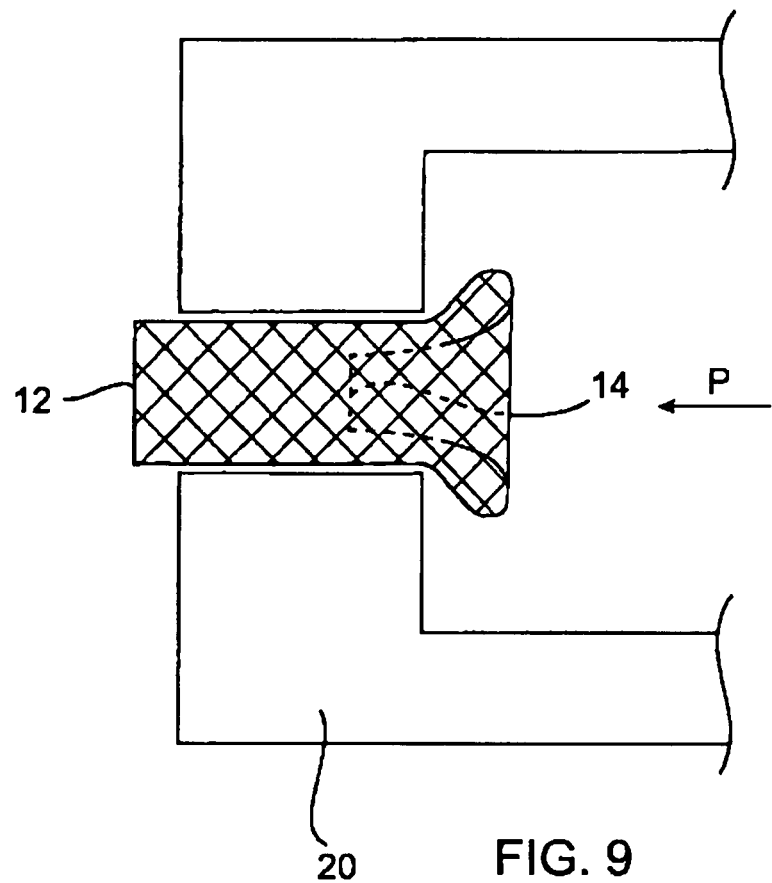
FIG. 9 is a sectional side elevation view of the mesh of FIG. 1 in a first position.
Figure 10:
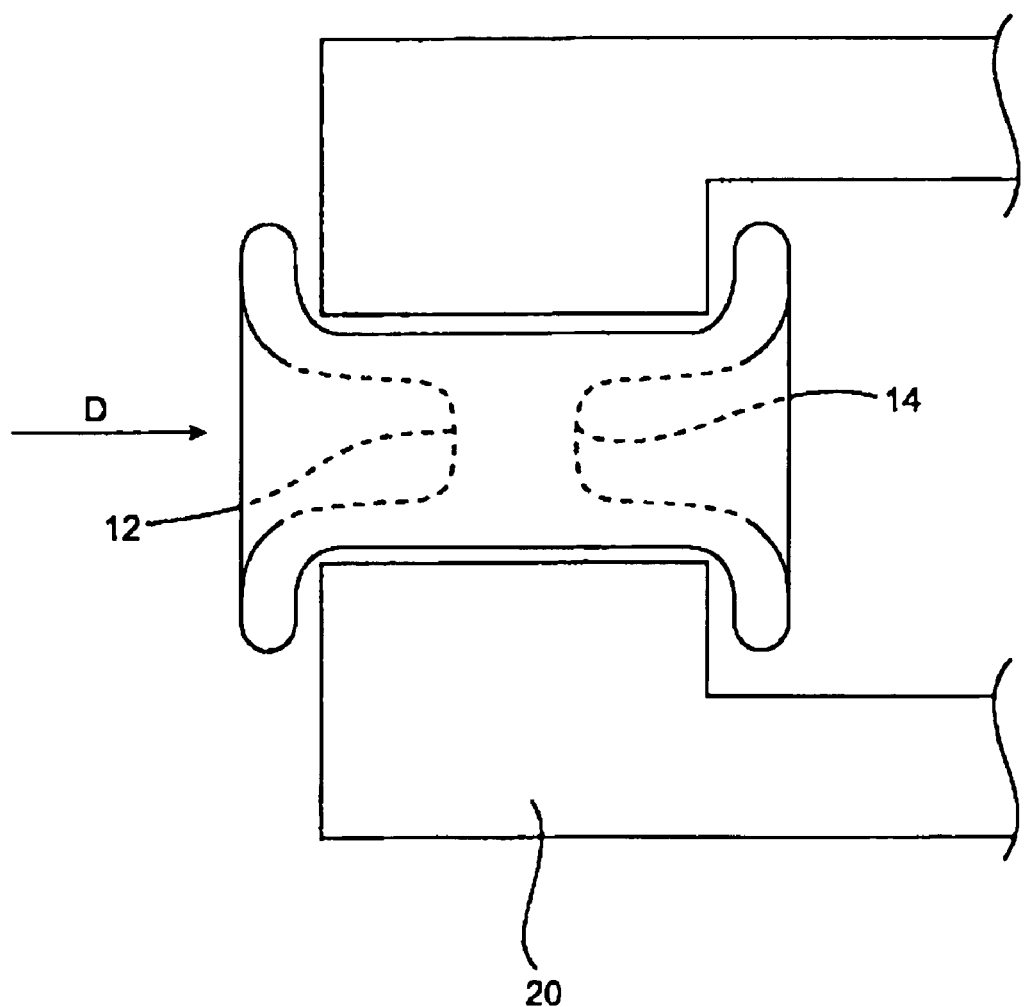
FIG. 10 is a sectional side elevation view of the mesh of FIG. 1 in a second position.

In another aspect of the invention, as illustrated in FIGS. 9 and 10, each of the proximal and distal ends of the cylindrical mesh may be pulled inwardly towards the longitudinal center of the cylindrical mesh such that the proximal end is moved distally and the distal end is moved proximally, as follows.

FIG. 9 shows a sectional elevation view of the mesh of FIG. 1 in a first position wherein distal end 14 has been pulled partially through the center of the cylindrical mesh 10 such that distal end 14 is received within the central body portion of mesh 10. Thereafter, as shown in FIG. 10, proximal end 12 is then pushed partially through the center of the cylindrical mesh 10 such that proximal end 12 is also received within the central body portion of mesh 10.

In the aspect of the invention shown in FIGS. 9 and 10, mesh 10 will especially tend to expand radially at outer surface 11 and inner surface 13 close to ends 12 and 14 as shown. Expansion of mesh 10 in these regions will cause formation of bulges immediately outside of the distal and proximal ends of hole 21 as shown. Such bulges will tend to anchor the mesh such that it does not move longitudinally in hole 21. In the aspect of the invention shown in FIGS. 9 and 10, both proximal end 12 and distal end 14 may optionally be covered by mesh or end caps since these ends need not pass through one another.

In this and the above discussed aspects of the invention, outward radial forces of the portions of the mesh which are curled within the main body of the mesh will preferably act against the outside walls of the outer tube creating frictional loads along the longitudinal axis that far exceed the unfolding tendency of the mesh.

A further advantage of the present invention is that it may be adapted to compensate for both thick or thin annular walls. For example, should the length of hole 21 be slightly longer than the length of mesh 10, ends 12 and 14 will still be fully engaged within hole 21. Another advantage of the present invention is that the exposed portions of the mesh projecting out of hole 21 (e.g.: bulges 15 and 17) will be atraumatic, minimizing any potential irritation due to tissue contact due to the soft and flexible nature of the mesh.

Figure 11:
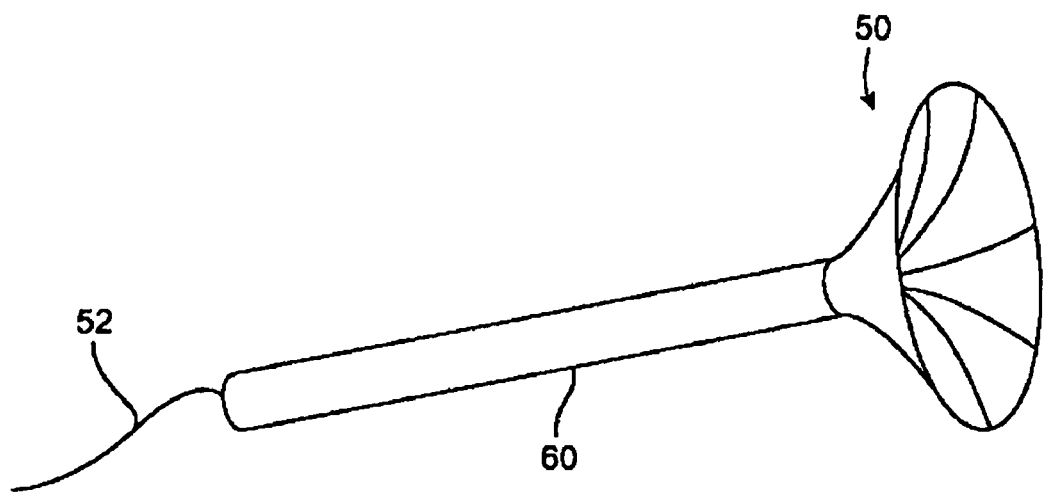
FIG. 11 is a perspective view of an alternate aspect of the first embodiment of the present invention.
Figure 12A:
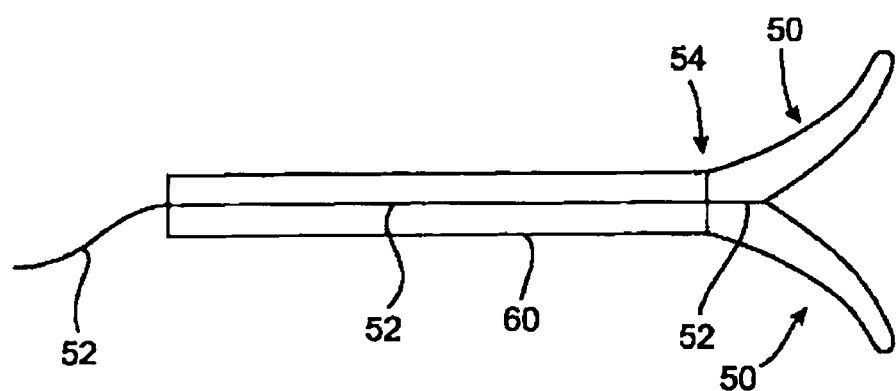
FIG. 12A is a sectional side elevation view of the system of FIG. 11 positioned in the annular hole.
Figure 12B:
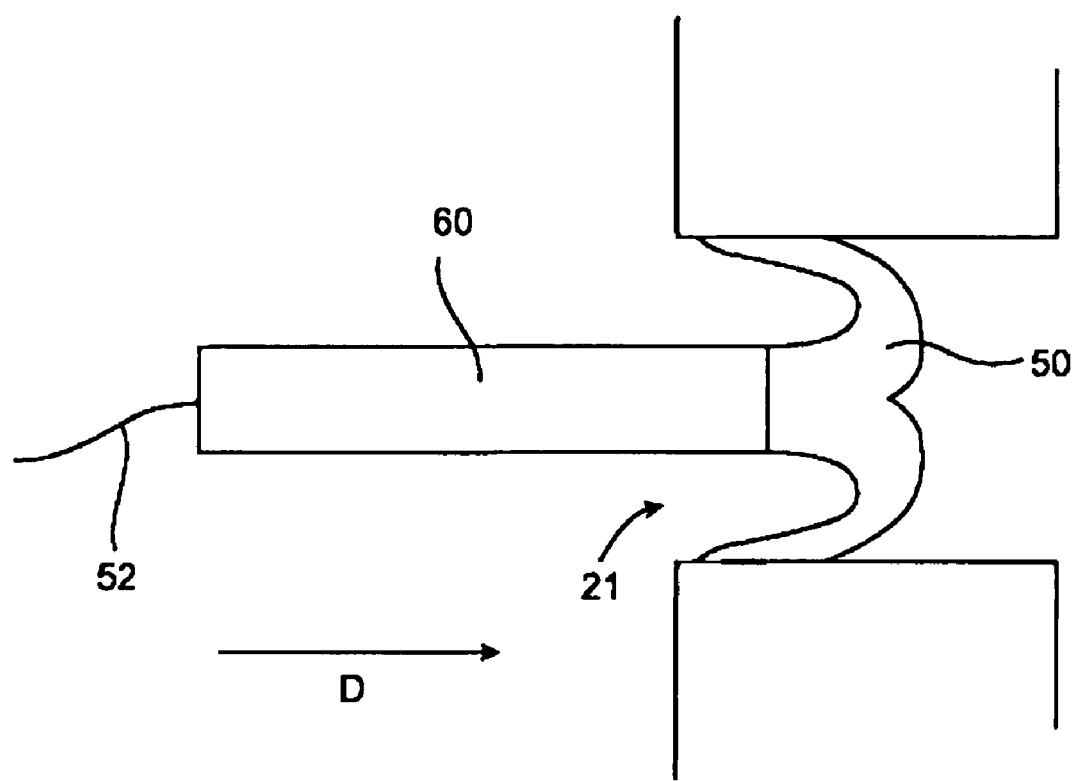
FIG. 12B is a side elevation view corresponding to FIG. 12A, but with the system distally advanced into the hole.

An alternate aspect of the first embodiment of the present invention is shown in FIGS. 11 to 12B, as follows. A mesh 50, (similar in characteristics to mesh 10 as described above), is provided. As seen in the cross sectional view of FIG. 12A, a suture/tether 52 runs from distal end 54 through the center of installation tube 60. As mesh 50 is advanced distally into hole 21, as shown in FIG. 12B, it will form a "reversing funnel" shape with the outer edges of mesh 50 wrapping over the body of the mesh inserted therethrough.

Figure 13A:
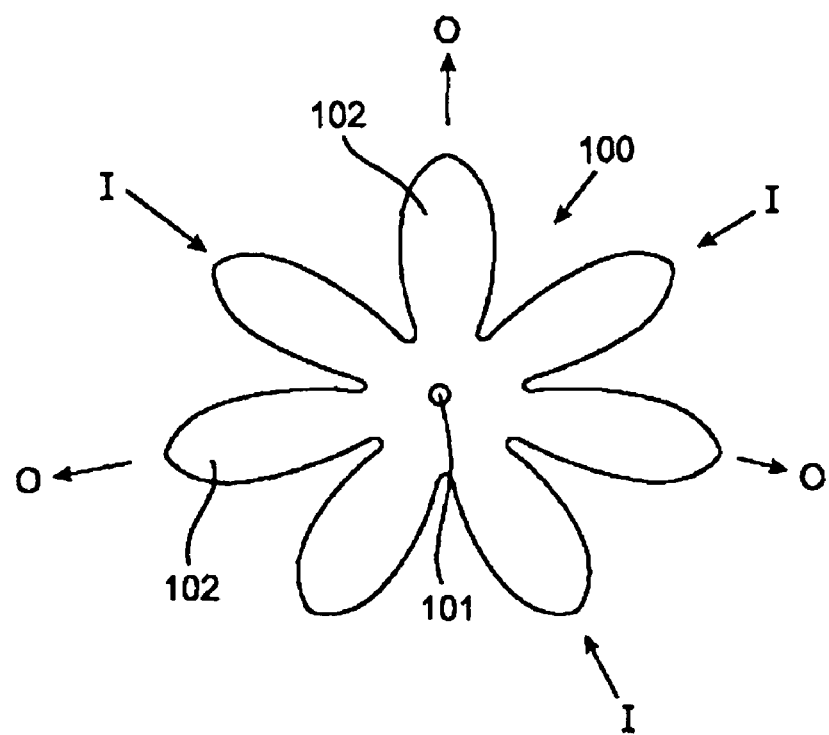
FIG. 13A is a front elevation view of a second aspect of the present invention.
Figure 13B:
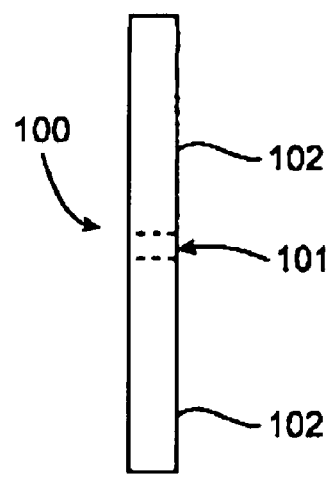
FIG. 13B is a side elevation view of the device of FIG. 13A.

FIGS. 13A and 13B show respective front and side views of a second design of the present invention in which device 100 comprises a generally planar sheet of material which is cut or formed in a circular shape, having a plurality of radially extending "flower petal" extensions 102. These devices allow pressure equalization through the venting of lower viscosity fluids but retain higher viscosity fluids and solids.

Figure 14:
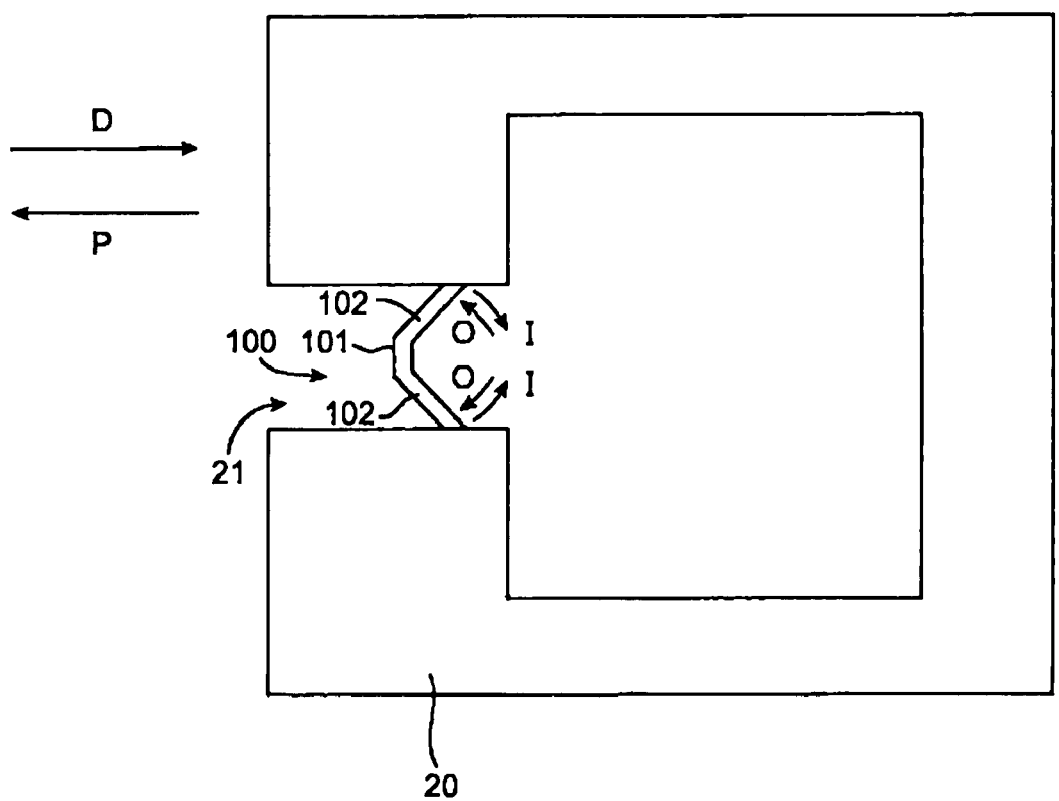
FIG. 14 is a side elevation view of the system of FIGS. 13A and 13B deformed into a conical shape and inserted into a surgical access hole in an intervertebral disc.

When inserted into a surgical access hole, petals 102 are first flexed radially inward in direction I. Accordingly, sheet 100 assumes a generally conical shape when inserted into hole 21 in intervertebral disc 20, as is shown in FIG. 14. After device 100 has been positioned in hole 21, (for example with a rod), petals 102 are released. Accordingly, petals 102 will tend to "spring back", moving radially outwards in direction O such that petals 102 will press against the outer surfaces 22 of hole 21 thereby anchoring device 100 in position in hole 21. As such, petals 102 act as cantilever leaf springs anchoring device 100 in position in hole 21, thereby resisting outward (i.e. proximal) loading due to extruding nucleus pulposus.

Figure 15:
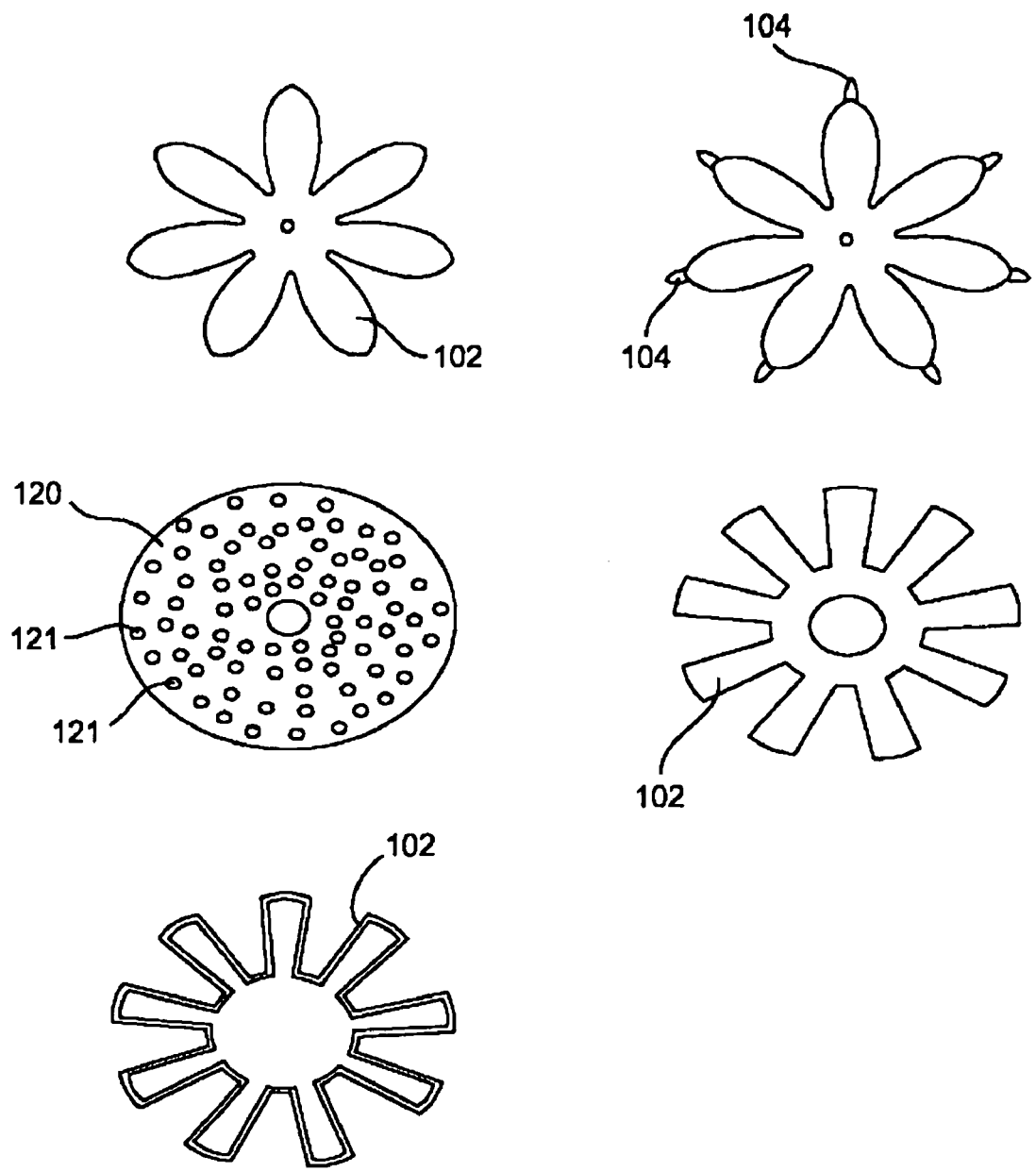
FIG. 15 is a front view of different designs for the second aspect of the present invention shown in FIGS. 13A and 13B.

As is shown in FIG. 15, optional barbs 104 may also be provided at the distal ends of petals 102 to assist in anchoring petals 102 of device 100 against walls 22 of hole 21. FIG. 15 shows a variety of alternate designs with differently shaped petals 102. FIG. 15 also shows an optional design for a sheet 120 which does not have petals. Rather, such a sheet is preferably crimped into a conical shape such that it can be positioned in hole 21. Thereafter sheet 102 will expand (ie: flatten itself) to seal hole 21 with holes 121 allowing for fluid movement similar to the movement permitted between adjacent petals 102 as shown in other aspects of the invention.

Device 100 may preferably by formed to accommodate hole 21 having an inner diameter ranging from one-half to three quarters of the disc diameter in its free and flattened state. Device 100 can be formed from wire or molded from plastic.

Figure 16:
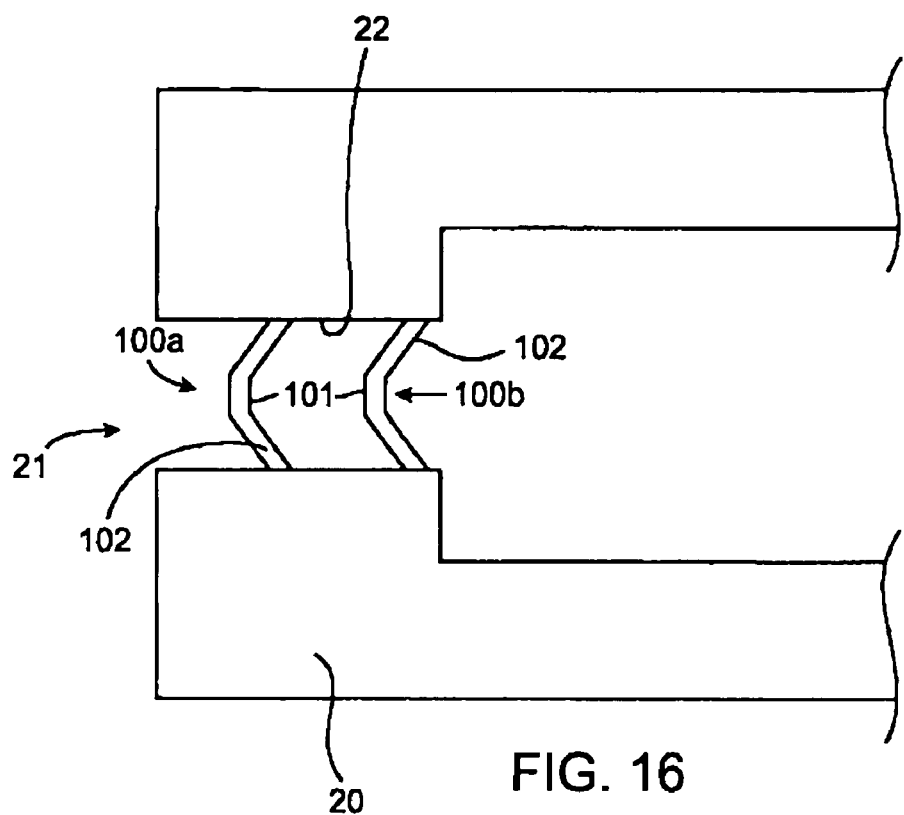
FIG. 16 is a side elevation view of a plurality of devices as illustrated in FIG. 13A, 13B or 15 deformed into conical shapes and inserted into a surgical access hole in an intervertebral disc.
Figure 17:
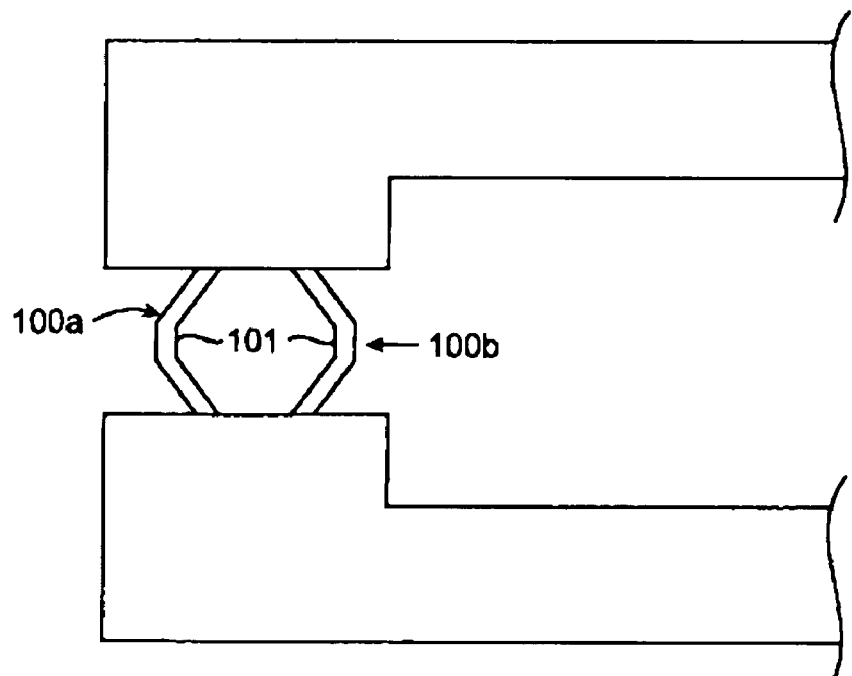
FIG. 17 corresponds to FIG. 16 but illustrates the apexes of the conical shapes pointing in opposite directions.

In preferred aspects, a plurality of devices 100 can be inserted into hole 21 in sequence as shown in FIG. 16. Such an arrangement has the advantage of further restricting the movement of nucleus pulposus out of the center of disc 20. FIG. 17 corresponds to FIG. 16 but with the apexes 101 of devices 100a and 100b pointing in opposite directions.

Figure 18:
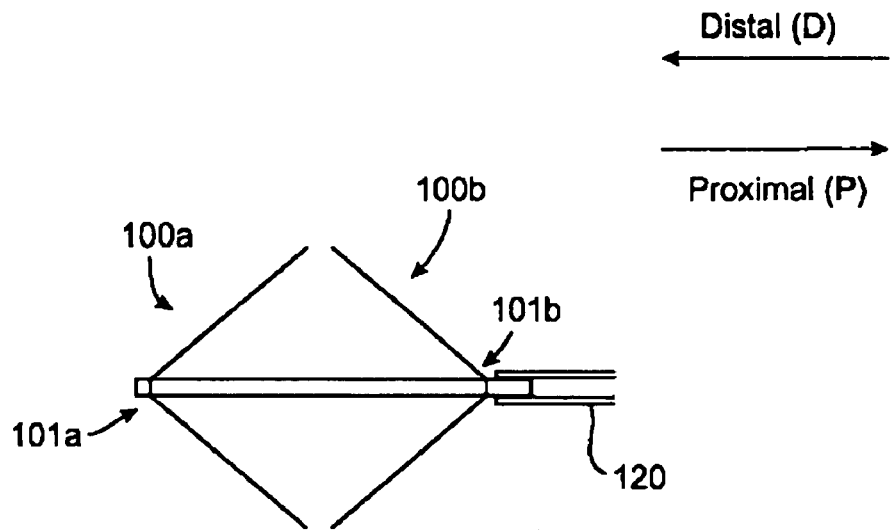
FIG. 18 is a side elevation view of a pair of systems as illustrated in FIG. 13A, 13B or 15 for insertion into a surgical access hole in oppositely facing directions.
Figure 19:
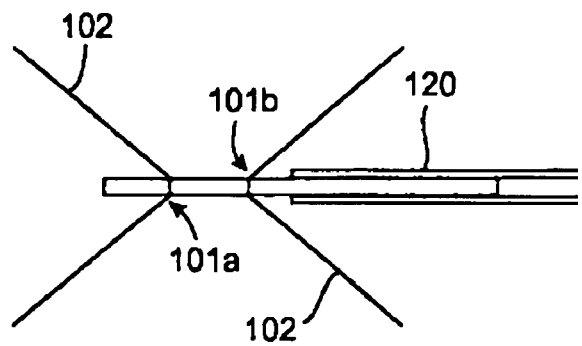
FIG. 19 shows a side view of the system arrangement of FIG. 18, but with the conical shaped structures deformed into an inverted position.
Figure 20:
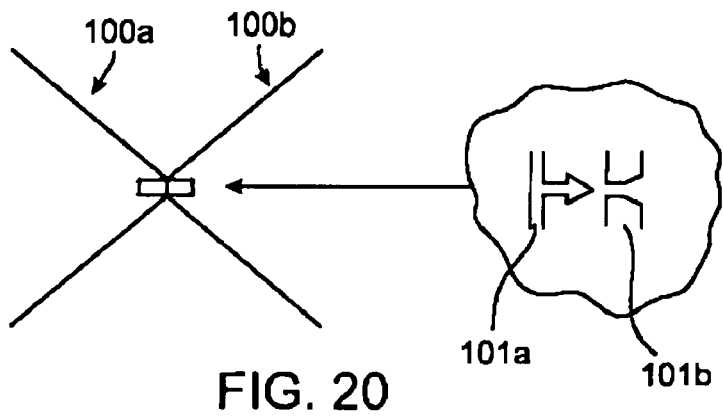
FIG. 20 shows a side view and an enlarged close-up view of the conical shaped structures of FIGS. 18 and 19 interlocked together.

FIGS. 18, 19 and 20 show successive steps in a method of inserting oppositely facing interlocking devices 100. Referring to FIG. 18, discs 100a and 100b are first introduced into hole 21 (not shown) in an orientation such that their apexes 101a and 101b are pointing in opposite directions. A positioning rod 120 is used to push devices 100a and 100b together such that devices 100a and 100b become inverted such that their apexes 101a and 101b will be pushed together. As is seen in FIG. 20, apexes 101a and 101b can comprise interlocking features such that they can be assembled to interlock together thereby forming a solid structure which tends to reduce radial movement of the respective apexes.

Experimentally Developed Embodiments

The Applicants of the present invention have succeeded in constructing various experimental embodiments of the present invention, as follows. These experimental embodiments are meant to illustrate various exemplary systems in accordance with the present invention. The present invention is not limited to the experimental embodiments described herebelow. Rather, any suitable system for achieving the structures and methods of the present invention as claimed is considered within the scope of the present invention.

Mesh 10 of the present invention was experimentally constructed as a braided tube approximately 3 mm in diameter when in the relaxed state, and at least 9 mm in diameter when expanded. This tube was be braided from 24 individual strands of 0.15 mm polypropylene suture. Alternatively, however, various numbers of strands may employed in the braiding of the tube.

An experimental embodiment of mesh 10 was constructed from a 45 mm length of braid which is cut and then placed over a heat resistant mandrel that just fits inside of the braid. The mandrel may preferably be fabricated from a machineable ceramic. A 12 mm long stainless steel tube whose inside diameter just fits over the braid may be placed over the braid/mandrel assembly with approximately 1 mm of braid exposed over the mandrel. The braid/mandrel/tube assembly was then placed in a lathe chuck or other machine capable rotating the assembly about it's longitudinal axis in a controlled manner. The end of the braid was then radiantly heated to just past the melting point of the braid polymer. The braid end was reformed to create a semi-rigid ring with in inside diameter of approximately equal to the original inside diameter of the braid. By using this non-contact method of forming using radiant heat and the fluidic surface tension of the re-flowing polymer, a robust and smooth unitary ring was quickly formed. The whole assembly was then removed from the rotating machinery. The first mandrel was removed from the assembly and a second forming mandrel was inserted in it's place. The second forming mandrel was made of a machineable ceramic material, and one end of the mandrel being formed with a tapered bullet shaped tip. The bullet tip was placed even with the tapered tip at the end of the proximal end of the braid. The 12 mm long stainless steel tube was then placed over the braid/mandrel assembly with approximately 1 mm of braid exposed over the bullet tipped mandrel. The braid/mandrel/tube assembly was again placed in the rotating machinery and slowly rotated about its longitudinal axis. The proximal end of the braid was then radiantly re-flowed to form a semi-rigid ring with an inside diameter of approximately one half to one quarter of the original braided diameter. The forming process described above can be accomplished in many different ways using a variety of equipment and techniques. Alternatively, rings of non-native material may have instead been secondarily added to the braided tube. The braid was then removed from the forming tools. A long piece of suture was then transversely passed through at least one braid intersection located near the distal end of the device. The tag ends of the suture are then brought together to form a loop with the device near the approximate center of the suture. This loop forming procedure is repeated twice more to form a system of three equally spaced suture loops with a radial spacing of about 120° when viewed from the end. The braid/loop assembly was then placed at the distal end of a long rod or tube whose outside diameter will allow for the longitudinal urging of the proximal end of the device and still allow for diametral clearance of at least two wall thickness of the braid material. The loops of suture were placed along side the length of the urging rod and arranged in a manner to prevent tangling of the tag ends. A second long hollow tube with an outside diameter that allows for passage into the surgical defect and inside diameter that allows for a slight diametral compression of the braid/loop assembly, is passed over the braid/loop assembly until approximately 4 mm of braid is exposed. It is to be understood that appropriate handles, grips and controls may also be added to the installation tool to enhance placement of the device and ease of use.

While the present invention has been shown and described in terms of preferred embodiments thereof, it should be understood that this invention is not limited to any particular embodiment, and that changes and modifications may be made without departing from the true spirit and scope of the invention as defined in the appended claims.

What is claimed is:

1. A method for repairing a vertebral annulus having an aperture formed therein, comprising:

introducing a blocking element situated on the end of an insertion rod through at least a portion of said aperture such that a plurality of tethers attached to said blocking element extend proximally out of said hole along said insertion rod, said blocking element having a first length, and said insertion rod being disposed through an insertion tube and moveable relative to said insertion tube; and moving said insertion rod and said insertion tube relative to each other to radially expand at least a portion of said blocking element such that said blocking element has a second length shorter than said first length and said expanded portion of said blocking element blocks said aperture, said expanded portion of said blocking element being positioned beyond an inner surface of said annulus in an interior annular space to block said aperture.

2. The method of claim 1, wherein said blocking element is generally cylindrical in shape.

3. The method of claim 1, wherein said blocking element is generally conical in shape.

4. The method of claim 1, wherein said blocking element is comprised of surgical mesh.

5. The method of claim 4, wherein said surgical mesh is comprised of braided multifilliar strands of suture-type material.

6. The method of claim 5, wherein said suture-type material is plastic.

7. The method of claim 1, wherein said aperture comprises one of a surgical access hole and a naturally occurring hole.

8. The method of claim 1, wherein said expanded portion contacts the inner surface of the annulus around a perimeter of said aperture.

9. The method of claim 8, wherein a second expanded portion is positioned exterior to said annulus to block said hole.

10. The method of claim 1, wherein a second expanded portion is positioned exterior to said annulus to block said hole.

11. The method of claim 1, wherein said radial expansion occurs when a distal end of said blocking element is moved towards a proximal end of said blocking element.

12. The method of claim 11, wherein said distal end is moved towards said proximal end by pulling said plurality of tethers proximally.

13. The method of claim 1, wherein said plurality of tethers are attached to a distal end of said blocking element.

* * * * *